(12) United States Patent
Gilbert

(10) Patent No.: US 11,278,443 B2
(45) Date of Patent: Mar. 22, 2022

(54) APPARATUS FOR MAINTAINING OPEN NASAL AIRFLOW

(71) Applicant: William Gilbert, Weeki Wachee, FL (US)

(72) Inventor: William Gilbert, Weeki Wachee, FL (US)

( * ) Notice: Subject to any disclaimer, the term of this patent is extended or adjusted under 35 U.S.C. 154(b) by 93 days.

(21) Appl. No.: 16/594,726

(22) Filed: Oct. 7, 2019

(65) Prior Publication Data

US 2021/0100675 A1    Apr. 8, 2021

(51) Int. Cl.
*A61F 5/00* (2006.01)
*A61F 5/08* (2006.01)

(52) U.S. Cl.
CPC ...................... *A61F 5/08* (2013.01)

(58) Field of Classification Search
CPC .. A61F 5/08; A61M 29/00; A61M 2210/0618
See application file for complete search history.

(56) References Cited

U.S. PATENT DOCUMENTS

| | | | | |
|---|---|---|---|---|
| 851,048 A | * | 4/1907 | Woodward | A61F 5/08 606/199 |
| 1,077,574 A | * | 11/1913 | Woodward | A61F 5/08 606/199 |
| 1,255,578 A | * | 2/1918 | Boxley | A61F 5/08 606/199 |
| 1,481,581 A | * | 1/1924 | Woodward | A61F 5/08 606/199 |
| 2,681,652 A | * | 6/1954 | Laxton | A61F 5/08 128/858 |
| 4,759,365 A | | 7/1988 | Askinazy | |
| 5,727,543 A | * | 3/1998 | Corsaro | A61F 5/08 128/200.24 |
| 5,895,409 A | | 4/1999 | Mehdizadeh | |
| 6,270,512 B1 | | 8/2001 | Rittmann | |
| D540,462 S | | 4/2007 | Groeneveld | |
| 2006/0260613 A1 | | 11/2006 | Pinter | |
| 2006/0266367 A1 | | 11/2006 | Noce | |
| 2010/0063532 A1 | | 3/2010 | Moore | |

* cited by examiner

*Primary Examiner* — Steven O Douglas

(57) ABSTRACT

The intention of this invention, a nasal dilator, is disclosed for internal positioning within each single nostril, providing an unobstructed through air passage, between the Maxilla and the exterior septal cartilage. An open framework is disclosed for positioning internally within and dilating both nostrils together, and is constructed as two connected elongated loops, having two posterior ends extending beyond the bone structure, or, Maxilla, and two anterior ends, connected by the convex handle. Since every nostril is sensitive, and has unique dimensions, even on the same person, and the septum can be wider or narrower, the device material is flexible, but upon squeezing or expanding the posterior ends of the elongated loop ends or of the connecting member-convex handle, by finger pressure, the device will retain an altered flexible shape, to increase or decrease the nasal openings for comfort, as desired.

6 Claims, 1 Drawing Sheet

APPARATUS FOR MAINTAINING OPEN NASAL AIRFLOW

CROSS-REFERENCE TO RELATED APPLICATIONS

This application claims the benefit of U.S. Provisional Application No. 62/742,996 filed Sep. 17, 2019.

FIELD OF THE INVENTION

Embodiments of the present invention generally relate to an apparatus that supports and maintains an open nasal airflow during breathing.

BACKGROUND OF THE INVENTION

Many people's nostril structure is thinner than required, or misshapen, so the nostril sides may collapse during breathing or exercising—from inhalation, or while sleeping—from gravity, thus, causing mouth-breathing or sleep apnea.

The nasal dilator disclosed is provided in various sizes to fit and be retained in within a person's nostrils. The device functions to support and dilate the nasal passages to allow easier breathing during strenuous exercise, routine activities, or sleep. The dilator of the present invention is a simple open framework of two, non-toxic, non-abrasive, compliant, adjustable, elongated loops, inserted into the nostrils, and is retained in place by gentle pressure and friction between the nasal walls and the interior and exterior contact surfaces of the elongated loops.

Prevention of deep nasal insertion is provided by the down-turned contact surface of the external handle of the dilator, connecting the two elongated loops, which is inserted until the contact surface of the handle rests against the exterior septal cartilage and also serves as a handle for insertion and removal. The material is preferably made of a flexible plastic, to maintain comfortable nasal support, yet, with finger pressure, can be bent narrower and hold that new shape, for immediate custom fitting to unique nostril widths, at the elongated loop ends.

The length extends the dilator internally under and beyond the nasal bone, Maxilla, into the nasal chamber, to extend the open airway, to better hold position, and to resist falling out.

DESCRIPTION OF THE PREFERRED EMBODIMENTS

Figure 1:
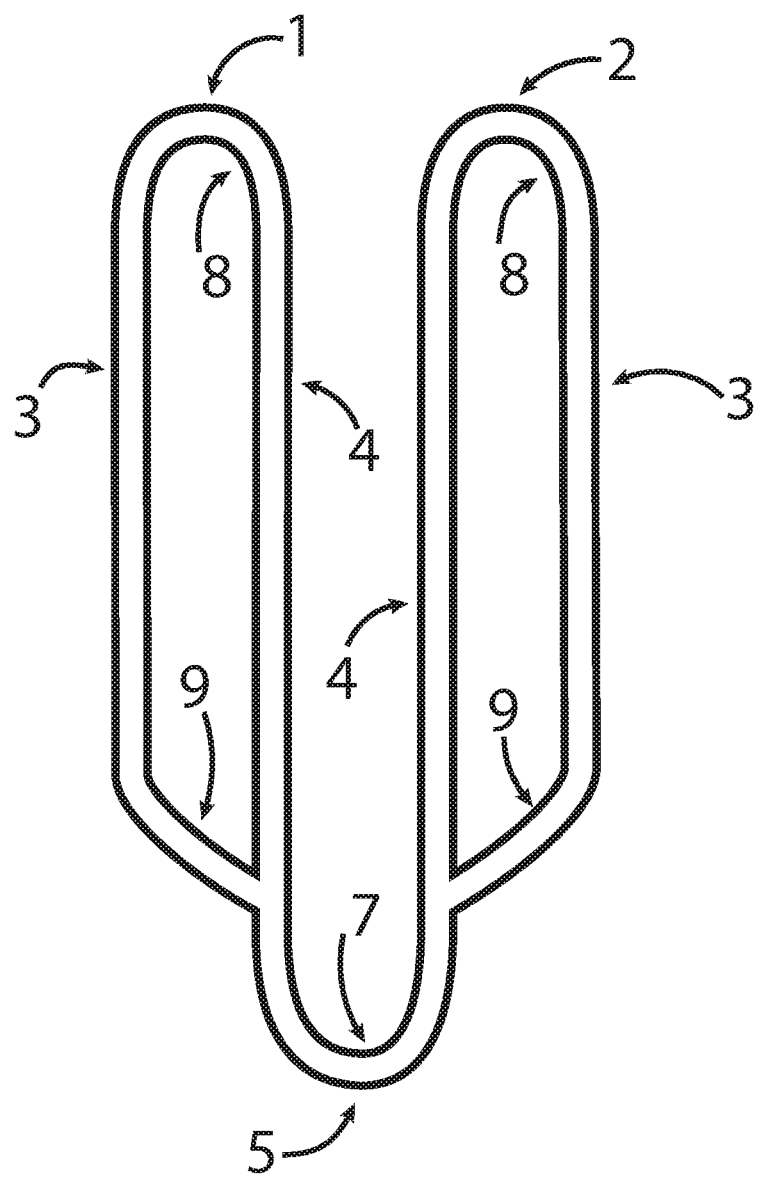
FIG. 1, below, is a top view of one embodiment of the present invention.
Figure 2:
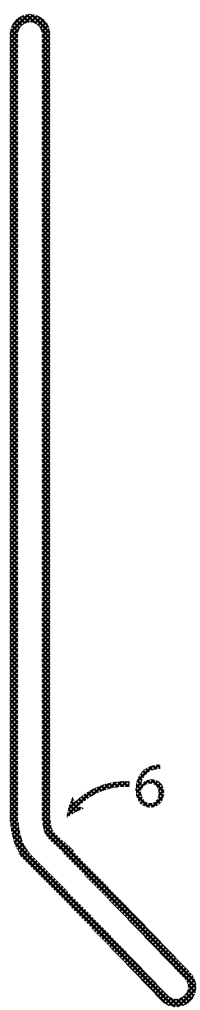
FIG. 2, below, is a side view of the present embodiment. Numbered parts identify Claimed descriptions.

The invention is in the form of a simple, open framework with no internal members which would impede airflow, and to ease cleaning of the dilator.

A First-1—and Second-2—Elongated Loop member, providing an Exterior-3—and Interior-4—Contact Surface; connected to a Convex Handle-5—that is angled approximately 135 Degrees-6—in relation to the plane of said first and second loop members; Wherein said convex handle further comprises Contact Surface-7—that abuts the Outer Septum of the user's nose. The first and second elongated loop members each further comprise a tapered Posterior End-8—which connects said exterior and interior contact surfaces, further comprise a tapered Anterior End-9—which connects said exterior contact surface with said convex handle. The angle-6—may be modified from 135 Degrees to between 100 Degrees and 160 Degrees in relation to the plane of said first and second loop members.

The invention will provide improved breathing capability for persons by expanding the cross section of the nasal passages, or nostril propping, thereby increasing the capacity of gas (i.e., air, oxygen, anesthetic, etc.) inhaled by user. The invention is specifically targeted for persons who experience impeded breathing through the nose or who require greater breathing than usual. As aids to deep and increased breathing is useful in alleviating snoring and mouth breathing during exercise or sleep.

User comfort and safety is anticipated regardless of whether the device is used once, or long-term. The device disclosed herein is provided in four convenient sizes ranging from small, medium, large, and extra-large, to fit nostril sizes ranging from children to adults. Width of small nostril elongated loops would be 4 mm width opening, to large elongated loops at 7 mm width opening, with 4 mm septal width between elongated loops. Lengths of the device would range from 20 mm to 50 mm. The device minimizes contact with the nasal interior septum and sidewalls, for maximum comfort, in the sensitive nasal interior.

The device is made with an inert, low friction plastic, soft non-abrasive, resilient outer surface, flexible, yet upon forceful bending will adopt a new shape. Both elongated loops are connected by a downwardly angled, curved connecting, convex handle, such that, both connected nasal dilator elongated loops would be inserted simultaneously into both adjacent nostrils, until the contact surface of the convex handle touches to the base of the exterior septal cartilage, for proper positioning.

Although the best mode contemplated for carrying out the present invention has been shown and described herein, it will be understood that modification and variation may be made without departing from what is to be regarded to be the subject.

What is claimed:

1. A nasal dilator comprising:
    a first smooth shaped elongated loop member and a second smooth shaped elongated loop member having no convolutions to snag nasal tissue upon insertion and removal, wherein said first smooth shaped elongated loop member and said second smooth shaped elongated loop member each comprises an exterior contact surface and an interior contact surface, wherein said first smooth shaped elongated loop member and said second smooth shaped elongated loop member are shaped to glide smoothly into and out of a nasal passage; and
    a convex handle that is angled between 110 degrees to 160 degrees in relation to a plane of said first smooth shaped elongated loop member and said second smooth shaped elongated loop member, wherein said convex handle further comprises contact surface that is configured to abut an outer septum of a nose of a user.

2. The nasal dilator of claim 1 wherein said first smooth shaped elongated loop member and said second smooth shaped elongated loop member each further comprise a tapered posterior end which connects said exterior contact surface and said interior contact surface.

3. The nasal dilator of claim 1 wherein said first smooth shaped elongated loop member and said second smooth shaped elongated loop member each further comprise a tapered anterior end which connects said exterior contact surface with said convex handle.

4. The nasal dilator of claim 1 wherein said nasal dilator is made of a flexible material that permits said first smooth shaped elongated loop member and said second smooth shaped elongated loop member to contract and expand to maximize contact with an inner tissue of a nasal cavity of said user, wherein said nasal dilator is adjustable with pressure to accommodate narrower or wider nasal passages.

5. The nasal dilator of claim 2 wherein said tapered posterior end is configured to extend past a maxilla of said user and is approximately 5 centimeters long.

6. The nasal dilator of claim 1 wherein said convex handle is angled 135 degrees with respect to the plane of said first smooth shaped elongated loop member and said second smooth shaped elongated loop member.

\* \* \* \* \*